United States Patent [19]

Fleig et al.

[11] 4,218,460

[45] Aug. 19, 1980

[54] NITROIMIDAZOLES

[75] Inventors: Helmut Fleig, Mannheim; Helmut Hagen, Frankenthal; Toni Dockner, Meckenheim; Friedrich W. Kohlmann, Moorrege, all of Fed. Rep. of Germany

[73] Assignee: BASF Aktiengesellschaft, Fed. Rep. of Germany

[21] Appl. No.: 958,399

[22] Filed: Nov. 7, 1978

Related U.S. Application Data

[63] Continuation of Ser. No. 875,904, Feb. 7, 1978, abandoned, which is a continuation of Ser. No. 727,798, Sep. 29, 1976, abandoned.

[51] Int. Cl.² .................................... C07D 417/06
[52] U.S. Cl. .................... 424/270; 260/302 H; 260/302 D; 542/411
[58] Field of Search ............... 542/411; 260/302 H, 260/302 D; 424/270

[56] References Cited

U.S. PATENT DOCUMENTS

| | | | |
|---|---|---|---|
| 3,491,091 | 1/1970 | Berger et al. | 542/411 |
| 3,658,797 | 4/1972 | Ross et al. | 542/411 |
| 3,882,105 | 5/1975 | Garzia | 542/411 |
| 3,919,200 | 11/1975 | Berger et al. | 542/411 |
| 3,926,966 | 12/1975 | Hagen et al. | 260/302 D |
| 3,954,789 | 5/1976 | Cavalleri et al. | 542/411 |
| 3,984,426 | 10/1976 | Winkelmann et al. | 260/302 H |

OTHER PUBLICATIONS

Chemical Abstracts, 8th Collective Index, p. 30925s.

*Primary Examiner*—Arthur P. Demers
*Attorney, Agent, or Firm*—Keil & Witherspoon

[57] ABSTRACT

Nitroimidazolylvinylthiadiazoles, their production, and formulations containing same for use as chemotherapeutics in the treatment of microbial infections in humans and animals, especially of trichomoniasis, trypanosomiasis and amoebic dysentery.

15 Claims, No Drawings

NITROIMIDAZOLES

This is a continuation of application Ser. No. 875,904 filed Feb. 7, 1978, which was a continuation of Application Ser. No. 727,798 which was filed on Sept. 29, 1976. Both application Ser. Nos. 875,904 and 727,798 have now been abandoned.

This invention relates to nitroimidazolylvinylthiadiazoles, their production, and formulations containing same for use as chemotherapeutics in the treatment of microbial infections in humans and animals.

It is known that nitroheterocycles such as nitrofurans, nitrothiazoles and nitroimidazoles are effective as agents for treating bacteria, fungi and Protozoa. The minimum inhibition concentrations of prior art preparations, for example metronidazol or tinidazol, are of the order of between 0.1 and 2 ug/ml. However, their action and tolerance levels are not always satisfactory. There is therefore a need to synthesize new compounds with increased effectiveness.

We have now found that compounds of formula I

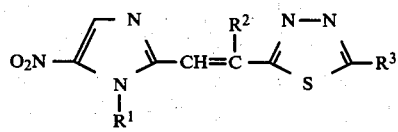

where $R^1$ is alkyl of 1 to 4 carbon atoms which may be substituted by hydroxy or alkoxy of 1 to 4 carbon atoms in the alkyl, $R^2$ is hydrogen or methyl, and $R^3$ is hydrogen, alkyl of 1 to 24 carbon atoms, unsubstituted or substituted phenyl, or hetroaryl have valuable pharmacological properties.

Examples of $R^1$ are methyl, ethyl, isopropyl, n-butyl, β-hydroxyethyl, β-methoxyethyl or β-ethoxyethyl.

Examples of suitable alkyl radicals of 1 to 24 carbon atoms for $R^3$ are methyl, ethyl, n-propyl, i-propyl, n-butyl, sec. butyl, isobutyl, amyl, n-hexyl, n-heptyl, n-octyl, 2-ethylhexyl, nonyl, decyl, undecyl, dodecyl, tridecyl, pentadecyl, octadecyl, cosyl, docosyl and tetradocosyl.

When $R^3$ is phenyl, the latter may be substituted once or several times, preferably once or twice, by radicals inert under the conditions of preparation. Special mention should be made of the following as inert substituents: halogen, such as fluoro, chloro, bromo, iodo, nitro and alkyl of 1 to 4 carbon atoms which in their turn may be substituted by one or more halogen atoms, such as trifluoromethyl, alkoxy of 1 to 4 carbon atoms, acylated and dialkylated amino groups each with 1 to 4 carbon atoms in the alkyl or acyl. Examples of substituted phenyl are 2-fluorophenyl, 4-fluorophenyl, 3-chlorophenyl, 2-bromophenyl, 3-bromophenyl, 4-iodophenyl, 2,4-dichlorophenyl, 3,5-dichlorophenyl, 2-methylphenyl, 3-ethylphenyl, 4-i-propylphenyl, 2,4-dimethylphenyl, 3,5-dimethylphenyl, 4-nitrophenyl, 3,5-dimethoxyphenyl, 4-dimethylaminophenyl, 4-trifluoromethylphenyl and 4-acetylaminophenyl.

Examples of suitable heteroaryl radicals for $R^3$ are pyridyl, furyl, thienyl, oxadiazolyl and thiadiazolyl.

Of the radicals mentioned above the following are preferred: for $R^1$ methyl, ethyl, β-hydroxyethyl, β-methoxyethyl and βethoxymethyl, for $R^2$ hydrogen and methyl, and for $R^3$ alkyl of 1 to 13 carbon atoms, of which alkyl of 1 to 6 carbon atoms and phenyl are particularly preferred; of the heteroaromatic radicals pyridine, which may be attached in the 2-, 3- or 4-position, is particularly preferred. Preferred substituted phenyl radicals are 2-chlorophenyl, 3-chlorophenyl, 4-chlorophenyl, 2-methylphenyl, 3-methylphenyl, 4-methylphenyl, 4-dimethylaminophenyl and 4-nitrophenyl.

Of these compounds those in which $R^1$ is methyl, $R^2$ is hydrogen or methyl and $R^3$ is hydrogen, methyl, ethyl, phenyl or pyridyl are particularly preferred.

The compounds of the invention may be prepared by reacting in known manner 2-substituted 1,3,4-thiadiazoles of the general formula II

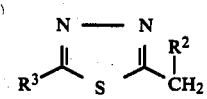

where $R^2$ and $R^3$ have the above meanings with a 5-nitroimidazole2-carboxaldehyde of the general formula III

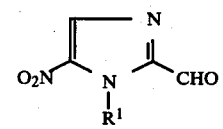

where $R^1$ has the above meanings at elevated temperatures and in the presence or absence of an acid condensation catalyst and in the presence or absence of a solvent. The aldehydes of formula III may also be used as acetals or acylals; special mention should be made here of acetals obtained from reactions with methanol and ethanol and the acylal obtained from reaction with acetic acid.

The reaction can be represented by the following equation

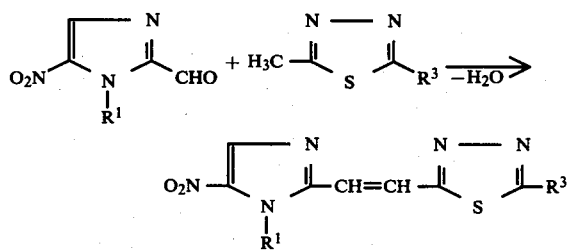

Some of the 1,3,4-thiadiazoles of formula II used as starting materials are known compounds or can be easily obtained for example by the process described by R. Stollé, Ber. dtsch. chem. Ges. 32, 797 (1899), in which N,N'-diacylhydrazines are reacted at elevated temperature with $P_2S_5$ in an aromatic hydrocarbon, e.g., xylene.

The compounds of the invention may be advantageously prepared by reacting a compound of formula II with a compound of formula III or its acetal or acylal at temperatures of between 50° and 220° C. preferably in the presence of an acid condensation catalyst, e.g. a Lewis acid, a mineral acid or an acid ion exchanger, and, if desired, in the presence of a solvent.

When a solvent is used the preferred temperature range is between 90° and 150° C., and when no solvent is used the preferred range is between 150° and 200° C.

Suitable catalysts are the acid condensation catalysts conventionally used in aldehyde condensation which are employed in amounts of 0.005 to 1 mole, preferably 0.05 to 0.2 mole, of catalyst per mole of starting material II. Examples of acid condensation catalysts are polyphosphoric acid, borofluoride and zinc chloride. The preferred catalyst is zinc chloride.

The starting materials are generally used in a stoichiometric ratio, although one of the compounds may be used in an excess. The reaction is generally carried out at atmospheric pressure, superatmospheric or subatmospheric pressure may however be an advantage in specific cases. The reaction may be effected in the presence or absence of a solvent. Solvents that have proved particularly suitable are lower carboxylic acids such as acetic acid and propionic acid, their anhydrides and mixtures of a lower carboxylic acid and the particular anhydride.

In the mixtures of carboxylic acid and carboxylic anhydride the ratio is advantageously between 9:1 and 1:9.

Generally the reaction is over within a few hours. Working up presents no problems; it can be effected for example by the addition of a precipitating agent, especially water or acetone, to the reaction mixture, precipitation of the reaction product, suction filtration, washing with water and alcohol, and recrystallization from a suitable solvent.

The following compounds are specified in addition to those described in the Examples:

2-thienyl-5-[2-(1-methyl-5-nitroimidazol-2-yl)-vinyl]-1,3,4-thiadiazole 2-n-propyl-5-[1-ethyl-2-(1-methyl-5-nitroimidazol-2-yl)-vinyl]-1,3,4-thiadiazole 2-ethyl-5-[1-methyl-2-(1-ethyl-5-nitroimidazol-2-yl)-vinyl]-1,3,4-thiadiazole 2-methyl-5-[2-(1-ethyl-5-nitroimidazol-2-yl)-vinyl]-1,3,4-thiadiazole 2-thienyl-5-[1-methyl-2-(1-methyl-5-nitroimidazol-2-yl)-vinyl]-1,3,4-thiadiazole 2-furyl-5-[2-(1-methyl-5-nitroimidazol-2-yl)-]1,3,4-thiadiazole   2-methyl-5-[2-(1-hydroxyethyl-5-nitroimidazol-2-yl)-vinyl]-1,3,4-thiadiazole 2-ethyl-5-[1-methyl-2-(1-hydroxyethyl-5-nitroimidazol-2-yl)-vinyl]-1,3,4-thiadiazole.

The compounds of the invention exhibit a good action on microorganisms. They are outstandingly effective for the treatment of infections by Flagellata, especially Trichomonas and Trypanosoma, and by Entamoaba histolytica in humans and animals.

They may also have a very good bacterial action in threshold concentrations of $<10^{-5}$, for example the compounds of Working Examples 6 and 7.

Table 1

Minimum inhibition concentrations (MIC) on Trichomonas vaginalis[1]

| Compound | MIC [µg/ml] | Relative effectiveness Metronidazol = 1.0 |
|---|---|---|
| Example 1 | 0.02 | 5.0 |
| Example 2 | 0.01 | 10.0 |
| Example 5 | 0.01 | 10.0 |
| Example 10 | <0.01 | >10.0 |
| Example 6 | <0.01 | >10.0 |
| Example 7 | <0.01 | >10.0 |
| Metronidazol | 0.1 | 1.0 |

Table 1-continued

Minimum inhibition concentrations (MIC) on Trichomonas vaginalis[1]

| Compound | MIC [µg/ml] | Relative effectiveness Metronidazol = 1.0 |
|---|---|---|
| Trinidazol | 0.1 | 1.0 |

[1]The tests were carried out in vitro using the quantitative tube-dilutiom test described by P. Klein, Bakteriologische Geundlagen der chemotherapeutischen Laboratoriumspraxis, Springer-Verlag Berlin-Coettingen-Heidelberg, 1957.

It is surprising that with the introduction of a thiadiazole radical attached via an ethylene bridge it has been possible to exceed the effectiveness of prior art commercial products, e.g., metronidazol and tinidazol, against Trichomonada infections up to more than ten times.

Special mention is made of the compounds of Examples 1,5, 7 and 10 for their action on Trichomonada.

The action against infections caused by Trypanosomas and *Entamoeba histolytica* can be illustrated on the mouse (NMRI strains) using methods described in Handbuch für experimentelle Pharmakologie, Ergänzungswerk 16, Erzeugung von Krankheitszuständen durch das Experiment, Part 9, pages 150 to 292, Springer-Verlag, Berlin-Goettingen-Heidelberg, 1964.

1. *Trypanosoma brucei*—infections of the mouse

Various dosages were investigated. The curing of the infection was determined microscopically and in a culture. There was also post-observation for 25 days after treatment was discontinued in order to establish whether there was any recidivation Example 1: 11×50 mg/kg perorally, acute 100% action, 70% recidivation
Example 2: 11×50 mg/kg perorally, no action
Example 5: 11×50 mg/kg perorally, no action
Example 10: 11×50 mg/kg perorally, acute 100% action, no recidivation
Example 6: 11×50 mg/kg perorally, no action
Example 7: 11×50 mg/kg, acute 100% action, 30% recidivation
Suramin: 7×50 mg/kg intraperitoneally, acute 80% action, no recidivation
Metronidazol: 11×50 mg/kg perorally, no action
Tinidazol: 22×50 mg/kg perorally, no action 2. Trypanosoma gambiense—infection of mouse Same method as in the case of *Trypanosoma brucei*

Example 1: 11×50 mg/kg perorally, acute 100% action, 80% recidivation
Example 2: 11×50 mg/kg perorally, no action
Example 5: 11×50 mg/kg perorally, no action
Example 10: 11×50 mg/kg perorally, acute 100% action, 60% recidivation
Example 6: 11×50 mg/kg perorally, no action
Example 7: 11×50 mg/kg perorally, no action
Suramin: 7×50 kg/mg intraperitoneally, acute 50% action, no recidivation 3. Trypanosoma congolense—infection of mouse Same method as in the case of *Trypanosoma brucei*

Example 1: 11×50 mg/kg perorally, acute 100% action, 20% no recidivation
Example 2: 11×50 mg/kg perorally, no action
Example 5: 11×50 mg/kg perorally, no action Example 10: 11×50 mg/kg perorally, acute 100% action, no recidication
Example 6: 11×50 mg/kg perorally, no action
Example 7: 11×50 mg/kg perorally, no action
Suramin: 7×50 mg/kg intraperitoneally, acute 70% action, no recidivation

4. Entamoeba histolytica (tube-dilution test)

The PN and Q strains were tested.
The minimum inhibition concentrations were as follows:
Example 1: <0.01 µg/ml
Example 2: 0.1 µg/ml
Example 5: <0.01 µg/ml
Example 10: <0.01 µg/ml
Example 6: <0.01 µg/ml
Example 7: <0.01 µg/ml
Mentronidazol: 0.1 µg/ml The experiments were carried out in vitro using the quantitative tube-dilution test described by P. Klein, Bakteriologische Grundlagen der chemotherapeutischen Laboratoriumspraxis, Springer-Verlag, Berlin-Goettingen-Heidelberg, 1957.

The results show that special mention should be made of the compounds of Examples 1 and 10 by virtue of their action and in comparison with Suramin, which is the constituent of the prior art preparations Germanin and Naganol. The action on Entamoeba histolytica in vitro can also be described as very good to good. As can be seen from the Table the action of metronidazol is surpassed more than 10 times.

5. Trichomonas vaginal—infection of mice

Various dosages were investigated. The curing of the infection was determined microscopically and in a culture.

Example 1: 100% with 5×25 mg/kg perorally
Example 2: 10% cure with 5×50 mg/kg perorally
Example 5: 100% cure with 5×25 mg/kg perorally
Example 10: 100% cure with 5×25 mg/kg perorally
Example 6: 50% cure with 5×50 mg/kg perorally
Example 7: 100% cure with 5×50 mg/kg perorally
Metronidazol: 100% cure with 5×25 mg/kg perorally
Tinidazol: 100% cure with 5×25 mg/kg perorally The LD 50 toxicity figures for the compounds of Examples 1, 7 and 10 on mice, NMRI strain, administered orally and with a week's observation period are over 1500 mg/kg.

The compounds of the invention can therefore be administered to humans and animals for therapeutic purposes for the treatment of trichomoniasis, trypanosomlasis and amoebic dysentery. They are also suitable for treating leishmaniasis.

Mention should be made of the following preferred active compounds:

2-phenyl-5-[2-(1-methyl-5-nitroimidazol-2-yl)-vinyl]-1,3,4-thiadiazole
2-(4-pyridyl)-5-[2-(1-methyl-5-nitroimidazol-2-yl)-vinyl]-1,3,4-thiadiazole
2-[2-(1-methyl-5-nitroimidazol-2-yl)-vinyl]-1,3,4-thiadiazole
2-ethyl-5-[2-(1-methyl-5-nitroimidazol-2-yl)-vinyl]-1,3,4-thiadiazole.

Particularly preferred compounds are:

2-methyl-5-[2-(1-methyl-5-nitroimidazol-2-yl)-vinyl]-1,3,4-thiadiazole and
2-ethyl-5-[1-methyl-2-(1-methyl-5-nitroimidazol-2-yl)-vinyl]-1,3,4-thiadiazole.

The present invention accordingly also relates to chemotherapeutic agents or formulations for treating microbial infections in humans and animals which contain a compound of formula I as active ingredient in addition to the conventional carriers and diluents, and also to the use of the new compounds for therapeutic purposes.

The chemotherapeutic agents or formulations are manufactured in a conventional manner using conventional carriers or diluents and the conventionally used pharmaceutical auxiliaries in accordance with the desired mode of administration in a suitable dosage unit.

The preferred formulations are suitable for oral administration. They may be in the form for example of tablets, coated tablets, dragees, capsules, pills, powders or suspensions. On account of the relatively sparing solubility of the compounds of the invention oral administration is preferred.

Naturally parenteral formulations, such as injection solutions, are also suitable. Suppositories are a further example of formulations that can be used. For the treatment of trichomoniasis pharmaceutical formulations for the vagina, such as vaginal tablets, globuli and powders, are also suitable.

The dose to be administered depends on the nature and the severity of the disorder. Amounts of up to 5 g per day may be administered.

Single doses to be administered several times a day if desired are advantageously 50 to 1000 mg per dose. In the case of Trypanosoma infections the single doses are advantageously between 500 and 1000 mg, in the case of Entamceba infections between 100 and 500 mg, and in the case of Trichomonada infections between 100 and 300 mg.

As a rule the single doses are administered from two to five daily and generally treatment of Trypanosoma infections lasts from 14 to 20 days, that of Entamoeba infections from 5 to 8 days, and that of Trichomonada infections also from 5 to 8 days.

For use in practice the compounds according to the invention can be processed with the carriers conventionally used in galenical pharmacy.

Tablets can be made for example by mixing the active ingredient with known auxiliaries, for example inert diluents such as dextrose, sugar, sorbitol, mannitol, PVP, calcium carbonate, calcium phosphate and lactose, disintegrants such as Indian corn, starch or alginic acid, binders such as starch or gelatines, lubricants such as magnesium stearate or talc, and/or agents for achieving a depot effect, such as carboxy polymethylene, carboxymethylcellulose, cellulose acetate phthalate or polyvinyl acetate. The tablets may also consist of a plurality of coatings.

Accordingly, dragees may be prepared by coating cores made in the same way as the tablets with agents conventionally used in dragee coatings, for example collidone or shellac, gum arabic, talc, titanium dioxide or sugar. The shell of the dragee may also consist of a plurality of coatings, and the auxiliaries mentioned above in connection with the tablets may be used.

Suspensions of the active ingredients according to the invention may also contain flavoring agents such as saccharine, cyclamate and sugar, and for example aromatics such as vanillin or orange extract. They may also contain auxiliaries that promote suspension such as sodium carboxymethylcellulose, and protective colloids such as p-hydroxybenzoates. Capsules containing active ingredients may be manufactured for example by mixing the active ingredient with an inert carrier such as lactose or sorbitol and encapsulating the mixture in gelatine capsules. Suitable suppositories may be manufactured for example by mixing the active ingredient with the appropriate carriers such as neutral fats or polyethylene glycol or derivatives thereof.

EXAMPLE 1

Preparation of
2-methyl-5-[2-(1-methyl-5-nitroimidazol-2-yl)-vinyl]-1,3,4-thiadiazole 11.4 g of 2,5-dimethyl-1,3,4-thiadiazole, 15.5 g of 1-methyl5-nitroimidazole-2-carboxyaldehyde with 0.2 g of zinc chloride are heated in a stirred apparatus for 10 hours at reflux temperature in a mixture of 50 ml of glacial acetic acid and 20 ml of acetic anhydride. After cooling, the precipitated solid is washed with glacial acetic acid and recrystallized from dimethylformamide. 15.6 g of colored crystals, Fp=248° C., is obtained, corresponding to 62% of the theory.

Example 2

2-phenyl-5-[2-(1-methyl-5-nitroimidazol-2-yl)-vinyl]-1,3,4-thiadiazole 17.6 g of 2-methyl-5-phenyl-1,3,4-thiadiazole, 15.5 g of 1-methyl-5-nitroimidazole-2-carboxaldehyde and 0.5 g of $ZnCl_2$ are heated in 100 ml of acetic acid and 50 ml of acetic anhydride for 7 hours at reflux temperature. After water has been added to the reaction mixture, the precipitated solid is recrystallized from glacial acetic acid. 17.5 g of a product melting at 257° C. is obtained, corresponding to 56% of the theory.

EXAMPLE 3

2-(2-chlorophenyl)-5-[2-(1-methyl-5-nitroimidazol-2-yl)-vinyl]-1,3,4-thiadiazole 21 g of 2-methyl-5-(2-chlorophenyl)-1,3,4-thiadiazole and 15.5 g of 1-methyl-5-nitroimidazole-2-carboxaldehyde are heated with 0.5 g of $ZnCl_2$ in a mixture of 100 ml of acetic acid and 50 ml of acetic anhydride for 6 hours at reflux temperature. After cooling, ether is added to the reaction mixture, and the precipitated solid is washed with water and recrystallized from dimethylformamide. 18.5 g of product is obtained, corresponding to 53% of the theory. The compound melts at 239° C.

EXAMPLE 4

2-(4-chlorophenyl)-5-[2-(1-methyl-5-nitroimidazol-2-yl)-vinyl]-1,3,4-thiadiazole 21 g of 2-methyl-5-(4-chlorophenyl)-1,3,4-thiadiazole and 22.8 g of 1-methyl-5-nitroimidazol-2-carboxaldehyde are heated with 0.5 g of $ZnCl_2$ in a mixture of 100 ml of acetic acid and 50 ml acetic anhydride for 5 hours at reflux temperature. After cooling, ether is added to the reaction mixture, and the precipitated solid is washed with water and recrystallized from dimethylformamide. 27.5 g of product of obtained, corresponding to 77% of the theory. The compound melts at 268° C.

Example 5

2-(4-pyridyl)-5-[2-(1-methyl-5-nitroimidazol-2-yl)-vinyl]-1,3,4-thiadiazole 8.8 g of 2-methyl-5-(4-pyridyl)-1,3,4-thiadiazole and 7.7 g of 1-methyl-5-nitroimidazole-2-carboxaldehyde are heated with 0.2 g of $ZnCl_2$ in a mixture of 50 ml of glacial acetic acid and 25 ml of acetic anhydride for 6 hours at reflux temperature. After cooling, the precipitated solid is suction filtered, washed with concentrated ammonia and recrystallized from dimethylformamide. The melting point of the product obtained is 240°–241° C.

2-[2-(1-methyl-5-nitroimidazol-2-yl)-vinyl]-1,3,4-thiadiazole 0.3 g of zinc chloride is added to 15.5 g of 1-methyl-5nitroimidazol-2-carboxaldehyde which has been dissolved in 100 ml of acetic acid and 50 ml of acetic anhydride and the whole is dripped into 10 g of 2-methyl-1,3,4-thiadiazole, which has been dissolved in a mixture of 100 ml of acetic acid and 50 ml of acetic anhydride, over a period of 5 hours at reflux temperature. After 24 hours the reaction mixture is freed of the solvent by evaporation and ether is added. After the reaction product has been washed with water it is recrystallized from xylene. 9.3 of product, corresponding to 39% of the theory, is obtained. The compound melts at 214° C.

EXAMPLE 7

2-ethyl-5-[2-(1-methyl-5-nitroimidazol-2-yl)-vinyl]-1,3,4-thiadiazole

A solution of 15.5 g of 1-methyl-5-nitroimidazole-2carboxaldehyde in 50 ml of acetic acid and 25 ml of acetic anhydride is added at reflux temperature over a period of 10 hours to 12.8 g of 5-ethyl-2-methyl-1,3,4-thiadiazole and 0.5 g of $ZnCl_2$ which have been dissolved in 100 ml of acetic acid and 50 ml of acetic anhydride. The mixture is kept at reflux temperature for a further 20 hours and the solvent is then evaporated. The residue is washed with acetone and passed through a ready-to-use silica gel column (Type A of Messrs. Merck) and eluted with $CHCl_3/CH_3OH=98:2$. 5.6 g of the abovementioned reaction product with a melting point of 165° C. is obtained; this corresponds to 21% of the theory.

EXAMPLE 8

2-methyl-5-[1-methyl-2-(1-methyl-5-nitroimidazol-2-yl)-vinyl]-1,3,4-thiadiazole

The acetone solution from Example 7 is concentrated, the residue passed through a ready-to-use silica gel column (Type A of Messrs Merck) and eluted with $CHCl_3/CH_3OH=98:2$. Yield 5.4 g, melting point 249° C. There is also obtained 3.4 g of the stereoisomeric compound with a melting point of 155° C.

The total yield from Examples 7 and 8 is 54% of the theory.

EXAMPLE 9

2-n-tridecyl-5-[2-(1-methyl-5-nitroimidazol-2-yl)-vinyl]-1,3,4-thiadiazole 8.45 g of 2-tridecyl-5-methyl-1,3,4-thiadiazole, 4.65 g of 1-methyl-5-nitroimidazole-2-carboxaldehyde and 0.5 g of zinc chloride are heated in 40 ml of acetic acid and 15 ml of acetic anhydride for 24 hours at reflux temperature. After the solvent has been removed, the residue is recrystallized from alcohol. 7.1 g of product is obtained, corresponding to 61% of the theory. The melting point is 91° C.

EXAMPLE 10

2-ethyl-5-[1-methyl-2-(1-methyl-5-nitroimidazol-2-yl)-vinyl]-1,3,4-thiadiazole 4.65 g of 1-methyl-5-nitroimidazole-2-carboxaldehyde, which has been dissolved in 80 ml of acetic acid and 35 ml of acetic anhydride, is dripped into 17.1 g of 2,5-diethyl-1,3,4thiadiazole, which has been dissolved in a mixture of 60 ml of acetic acid, 25 ml of acetic anhydride and 0.5 g of zinc chloride, over a period of 5 hours at reflux temperature. After being heated for a further 24 hours at reflux temperature the reaction mixture is concentrated by removing the solvent and water is added. The precipitated reaction product is then subjected to sublimation and recrystallized from propanol. 2.9 g of product, corresponding to 35% of the theory, is obtained. The compound melts at 125° C.

Examples of formulations prepared in conventional manner

1. Tablet

| 1. An active ingredient of formula I | 120 mg |
|---|---|
| Lactose | 200 mg |
| Methylcellulose | 15 mg |
| Cornstarch | 50 mg |
| Talc | 11 mg |
| Magnesium stearate | 4 mg |
| | 400 mg |
| 2. An active ingredient of formula I | 120 mg |
| Lactose | 178 mg |
| Avicel | 80 mg |
| Polywachs 6000 | 20 mg |
| Magnesium stearate | 2 mg |
| | 400 mg |

2. Vaginal tablet

| 1. An active ingredient of formula I | 80 mg |
|---|---|
| Lactic acid | 30 mg |
| Glucose | 670 mg |
| Lactose | 200 mg |
| Hydroxypropylmethylcellulose | 20 mg |
| | 1 g |
| 2. An active ingredient of formula I | 80 mg |
| Boric acid | 30 mg |
| Lactose | 890 mg |
| | 1 g |

3. Example of a tablet

| 1. Compound of Example 1 or Example 10 as active ingredient | 200 mg |
|---|---|
| 2. Polyvinylpyrrolidone (mean M.W. 25,000) | 20 mg |
| 3. Polyethylene glycol (mean M.W. 4,000) | 14 mg |
| 4. Hydroxypropylmethyl cellulose | 40 mg |
| 5. Talc | 4 mg |
| 6. Magnesium stearate | 2 mg |
| | 280 mg |

The active ingredient is moistened with polyvinylpyrrolidone in a 10% aqueous solution, passed through a sieve with 1.0 mm apertures and dried at 50° C. This granulated material is mixed with polyethylene glycol (mean M.W. 4,000) hydroxypropylmethylcellulose, talc and magnesium stearate and pressed into tablets à 280 mg.

4. Example of a dragée

| 1. Compound of Example 1 or Example 10 as active ingredient | 150 mg |
|---|---|
| 2. Lactose | 60 mg |
| 3. Cornstarch | 30 mg |
| 4. Polyvinylpyrrolidone | 4 mg |
| 5. Magnesium stearate | 1 mg |
| | 245 mg |

The mixture of active ingredient with lactose and cornstarch is granulated through a 1.5 mm sieve dried at 50° C. and then passed through a 1.0 mm sieve. The granulated material thus obtained is mixed with magnesium stearate and pressed into dragée cores. The latter are then covered in conventional manner with a coating consisting essentially of sugar and talc.

5. Example of a suppository

| 1 suppository contains | |
|---|---|
| Active ingredient | 250 mg |
| Suppository composition (e.g., Witepsol H 19) | 1500 mg |
| | 1750 mg |

The suppository composition is melted. At 38° C. the finely pulverized ingredient is dispersed homogeneously in the melt. It is then poured into precooled suppository molds at 35° C.

What we claim is:

1. Nitroimidazolylvinylthiadiazoles of the formula I

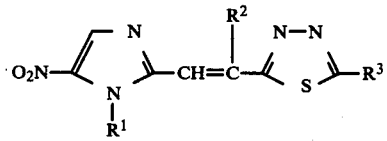

where $R^1$ is alkyl of 1 to 4 carbon atoms which may be substituted by hydroxy or alkoxy of 1 to 4 carbon atoms in the alkyl, $R^2$ is hydrogen or methyl, and $R^3$ is hydrogen, methyl, ethyl phenyl or pyridyl.

2. The compound of claim 1 wherein $R^1$ is methyl.
3. The compound of claim 1 wherein $R^3$ is methyl or ethyl.
4. The compound of claim 2 wherein $R^3$ is methyl.
5. The compound of claim 2 wherein $R^3$ is ethyl.
6. 2-methyl-5-[2-(1-methyl-5-nitroimidazol-2-yl)-vinyl]-1,3,4-thiadiazole.
7. 2-ethyl-5-[2-(1-methyl-5-nitroimidazol-2-yl)-vinyl]-1,3,4-thiadiazole.
8. 2-ethyl-5-[1-methyl-2-(1-methyl-5-nitroimidazol-2-yl)-vinyl]-1,3,4-thiadiazole.
9. 2-phenyl-5-[2-(1-methyl-5-nitroimidazol-2-yl)-vinyl]-1,3,4-thiadiazole.
10. 2-(4-pyridyl)-5-[2-(1-methyl-5-nitroimidazol-2-yl)-vinyl]-1,3,4-thiadiazole.
11. A chemotherapeutic composition useful in the treatment of trichomoniasis, trypanosomiasis and amoebic dysentery in humans and animals comprising a therapeutically effective amount of a nitroimidazolylvinyl-thiadiazole of the formula

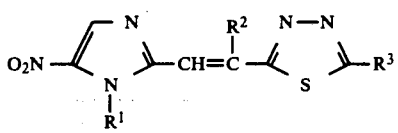

where $R^1$ is methyl, $R^2$ is hydrogen or methyl and $R^3$ is hydrogen, methyl, ethyl, phenyl or pyridyl, in a pharmaceutical carrier.

12. A chemotherapeutic composition as claimed in claim 11 wherein said nitroimidazolylvinylthiadiazole is 2-methyl-5-[2-(1-methyl-5-nitroimidazol-2-yl)-vinyl]-1,3,4-thiadiazole.

13. A chemotherapeutic composition as claimed in claim 12 wherein said nitroimidazolylvinylthiadiazole is 2-ethyl-5-[2-(1-methyl-5-nitroimidazol-2-yl)-vinyl]-1,3,4-thiadiazole.

14. A chemotherapeutic composition as claimed in claim 11 wherein said nitroimidazolylvinylthiadiazone is 2-ethyl-5-[1-methyl-2-(1-methyl-5-nitroimidazol-2-yl)-vinyl]-1,3,4-thiadiazole.

15. A chemotherapeutic composition as claimed in claim 11 containing said nitroimidazolylvinylthiadiazole in an amount providing 50 to 1,000 mg per dose.

* * * * *